United States Patent
He et al.

(10) Patent No.: US 10,556,835 B2
(45) Date of Patent: Feb. 11, 2020

(54) METHOD FOR POST-PROCESSING COLORED ZIRCONIUM OXIDE CERAMIC

(71) Applicant: Liaoning Upcera Dental Co., Ltd, Benxi, Liaoning (CN)

(72) Inventors: Lingling He, Liaoning (CN); Yanchun Zheng, Liaoning (CN); Ying Guo, Liaoning (CN)

(73) Assignee: LIAONING UPCERA DENTAL CO., LTD, Benxi, Liaoning (CN)

( * ) Notice: Subject to any disclaimer, the term of this patent is extended or adjusted under 35 U.S.C. 154(b) by 245 days.

(21) Appl. No.: 15/534,346

(22) PCT Filed: Sep. 22, 2015

(86) PCT No.: PCT/CN2015/090280
§ 371 (c)(1),
(2) Date: Jun. 8, 2017

(87) PCT Pub. No.: WO2016/090989
PCT Pub. Date: Jun. 16, 2016

(65) Prior Publication Data
US 2017/0341992 A1 Nov. 30, 2017

(30) Foreign Application Priority Data
Dec. 8, 2014 (CN) .......................... 2014 1 0742446

(51) Int. Cl.
| | | |
|---|---|---|
| C04B 41/85 | (2006.01) | |
| A61K 6/02 | (2006.01) | |
| C04B 35/48 | (2006.01) | |
| C04B 111/82 | (2006.01) | |
| C04B 41/00 | (2006.01) | |
| C04B 41/52 | (2006.01) | |
| C04B 41/89 | (2006.01) | |
| C04B 35/486 | (2006.01) | |
| A61K 6/04 | (2006.01) | |
| C04B 35/634 | (2006.01) | |
| C04B 35/636 | (2006.01) | |
| C04B 111/00 | (2006.01) | |

(52) U.S. Cl.
CPC .............. *C04B 41/85* (2013.01); *A61K 6/024* (2013.01); *A61K 6/043* (2013.01); *C04B 35/48* (2013.01); *C04B 35/486* (2013.01); *C04B 35/636* (2013.01); *C04B 35/63416* (2013.01); *C04B 35/63488* (2013.01); *C04B 41/009* (2013.01); *C04B 41/52* (2013.01); *C04B 41/89* (2013.01); *C04B 2111/00836* (2013.01); *C04B 2111/82* (2013.01); *C04B 2235/3224* (2013.01); *C04B 2235/3225* (2013.01); *C04B 2235/6562* (2013.01); *C04B 2235/663* (2013.01); *C04B 2235/77* (2013.01); *C04B 2235/9661* (2013.01)

(58) Field of Classification Search
CPC .................. C04B 35/48; C04B 35/486; C04B 2235/3244; C04B 35/64; C04B 2235/652; C04B 2235/3224; C04B 2235/3246; C04B 2235/6587; A61K 6/024
USPC .................................................. 264/671–673
See application file for complete search history.

(56) References Cited

U.S. PATENT DOCUMENTS

| | | | | |
|---|---|---|---|---|
| 2008/0085828 | A1* | 4/2008 | Khan | ................. A61C 13/0003 501/152 |
| 2012/0196244 | A1* | 8/2012 | Khan | ................... A61C 13/082 433/6 |
| 2013/0029840 | A1* | 1/2013 | Morikawa | ................ B01J 35/04 502/304 |
| 2013/0341812 | A1* | 12/2013 | Schechner | ........... A61K 6/0094 264/17 |

FOREIGN PATENT DOCUMENTS

| | | |
|---|---|---|
| CN | 1944334 A | 4/2007 |
| CN | 103113132 A | 5/2013 |
| CN | 103708830 A | 4/2014 |
| JP | 4-280864 | 10/1992 |
| JP | 2003-212652 | 7/2003 |

OTHER PUBLICATIONS

English language translation of Hong et al., "Studies on the color center of stabilized cubic zirconia crystals," Journal of Synthetic Crystals, Dec. 1987, pp. 300-306, vol. 16, No. 4. Translated Apr. 2019 by Schreiber Translations, Inc. (Year: 1987).*
Li et al. "X-ray absorption studies of zirconia polymorphs. II. Effect of Y2O3 dopant on ZrO2 structure." Physical Review B, vol. 48, No. 14 (Oct. 1, 1993) pp. 10 074-10 081. (Year: 1993).*
Hong et al., "Studies on the color center of stabilized cubic zirconia crystals," Journal of Synthetic Crystals, Dec. 1987, pp. 300-306, vol. 16, No. 4.
International Search Report dated Dec. 18, 2015 in International Application No. PCT/CN2015/090280.

* cited by examiner

Primary Examiner — Erin Snelting
(74) Attorney, Agent, or Firm — Saliwanchik, Lloyd & Eisenschenk

(57) ABSTRACT

A method for post-processing a colored zirconium oxide ceramic, the method comprising: putting the colored zirconium oxide ceramic along with a deoxidant into a heating device, conducting a firing process at a preset temperature, and a colorant containing $Pr^{3+}$ is used for the coloring, and the deoxidant is excessive with respect to a stoichiometric amount of oxygen in the heating device. The technical solution can completely replace $Fe^{3+}$ with $Pr^{3+}$ to color the zirconium oxide ceramic yellow.

6 Claims, No Drawings

METHOD FOR POST-PROCESSING COLORED ZIRCONIUM OXIDE CERAMIC

CROSS-REFERENCE TO RELATED APPLICATIONS

The present application is a national stage application of international Patent Application No. PCT/CN2015/090280, filed Sep. 22, 2015, which claims priority to Chinese patent application No. 201410742446.1, filed Dec. 8, 2014, the disclosures of each of which are incorporated herein by reference in their entirety.

TECHNICAL FIELD

The present invention relates to the field of zirconium oxide ceramic, and in particular to a method for post-processing a colored zirconium oxide ceramic.

BACKGROUND

Zirconium oxide ceramics have been widely used in the production of dental prostheses due to the good biocompatibility and excellent mechanical properties.

Before zirconium oxide ceramics are finally produced to be a dental prosthesis that can be used for patients, they generally need coloring, glazing processes and the like to ensure the color of finally produced dental prosthesis is close to the tooth color of the patients themselves.

In the prior art, there are mainly two methods for coloring the zirconium oxide ceramics. The first method is adding coloring oxides to the raw materials during the process of preparing zirconium oxide ceramics, thus obtaining the pre-shaded zirconium oxide ceramics. The second method is using coloring liquid to color the restorations of the patient, which is made from zirconium oxide pre-sintering body. The natural tooth shows a narrow range of color variance, and mainly appears to be red or yellow. Thus, no matter the colorant is the coloring oxide of the first method or the coloring agent of the second method, the contained coloring ions in which mainly contain $Fe^{3+}$, $Er^{3+}$, and $Mn^{2+}$ etc., wherein $Fe^{3+}$ is mainly for deepening yellow and red, $Er^{3+}$ is mainly for deepening red, and $Mn^{2+}$ is mainly for adjusting lightness. Since the radius and coordination number of $Fe^{3+}$ ion is different from those of $Zr^{4+}$, most of $Fe^{3+}$ ions in the zirconium oxide ceramics exist in crystal boundary, such that the transparency of the colored zirconium oxide ceramics will reduce tremendously.

Replacing $Fe^{3+}$ in the above-mentioned ions with $Pr^{3+}$ can increase the transparency of the colored zirconium oxide ceramics. However, coloring zirconium oxide ceramics by $Pr^{3+}$ instead of $Fe^{3+}$, after glazing and firing the colored zirconium oxide ceramics, it appears obviously lighter yellow compared with that before firing. Sometimes, porcelain veneering and the first firing are needed according to the requirement of the colored zirconium oxide ceramics; then glazing and the second firing are performed. In this way, after firing for several times, it allows the zirconium oxide ceramic to exhibit a much lighter yellow. Thus, $Fe^{3+}$ cannot be completely replaced with $Pr^{3+}$ for coloring zirconium oxide ceramic to be yellow at the present stage.

SUMMARY OF THE INVENTION

The present invention provides a method for post-processing a colored zirconium oxide ceramic to solve the problem that the zirconium oxide ceramic colored with $Pr^{3+}$ exhibits obviously much lighter yellow after firing compared with the color before firing.

The technical solution is as follow:

A method for post-processing colored zirconium oxide ceramic can comprise:

putting colored zirconium oxide ceramic along with a deoxidant into a heating device, and performing a firing process at a preset temperature, wherein the colored zirconium oxide ceramic is obtained by coloring a zirconium oxide ceramic with a colorant containing $Pr^{3+}$ and the amount of said deoxidant is over-stoichiometric with respect to the amount of oxygen in said heating device, wherein, said deoxidant is an organic or inorganic material which can react with oxygen in the heating device for removing oxygen in the heating device.

In particular, the deoxidant can be at least one of activated carbon, charcoal, starch, coal, saccharose, lactose, polyethylene glycol in powder form, polyvinyl alcohol, polyethylene, and polypropylene.

In one preferred embodiment of the present invention, before putting the colored zirconium oxide ceramic along with the deoxidant into the heating device and performing a firing process at a preset temperature, the method further comprises veneering porcelain or glazing on the zirconium oxide ceramic.

In one preferred embodiment of the present invention, the method of coloring the zirconium oxide ceramic with the colorant containing $Pr^{3+}$ comprises:

coloring the zirconium oxide ceramic with a coloring agent containing $Pr^{3+}$, or coloring the zirconium oxide ceramic by adding an oxide containing $Pr^{3+}$ into raw materials during the process of preparing the zirconium oxide ceramic.

In one preferred embodiment of the present invention, said coloring agent is UPCERA Coloring Liquid II.

In one preferred embodiment of the present invention, said heating device is a porcelain furnace.

It can be seen from the technical solution above that the technical solution of the present invention is achieved by putting the colored zirconium oxide ceramic along with a deoxidant into a heating device, performing a firing process at a preset temperature, wherein a colorant containing $Pr^{3+}$ is used for the coloring, and the amount of said deoxidant is over-stoichiometric with respect to the amount of oxygen in said heating device. During the process of firing, the deoxidant can eliminate oxygen in the heating device and prevent $Pr^{3+}$ converting into $Pr^{4+}$, thereby to solve the problem that the zirconium oxide ceramic colored with $Pr^{3+}$ exhibits obviously much lighter yellow after firing compared with the color before firing. It can be achieved completely replacing $Fe^{3+}$ with $Pr^{3+}$ to color the zirconium oxide ceramic as yellow by using technical solution of the present invention.

DETAILS OF THE INVENTION

In the prior art, coloring zirconium oxide ceramic by $Pr^{3+}$ instead of $Fe^{3+}$, after veneering porcelain or glazing and then firing the colored zirconium oxide ceramic, it appears obviously lighter yellow compared with the color before firing. Furthermore, firing several times will make yellow presented by zirconium oxide ceramic much lighter.

The inventors consult plenty of the prior art and find that no prior art can explain the reason for the problem mentioned above. After studying for a long time, without limiting to any theory, the inventors deduce that the main reason for the problem mentioned above lies in the oxygen present in the heating device during the process of firing. During the heating process of firing, the oxygen atom in oxygen will occupy the oxygen vacancies in the polycrystal of zirconium oxide, such that the oxygen vacancies will decrease in the polycrystal of zirconium oxide. It leads to that $Pr^{3+}$ is oxidized into $Pr^{4+}$, the oxide of $Pr^{3+}$ is yellow whereas the oxide of $Pr^{4+}$ is black. Thus, the decrease of $Pr^{3+}$ renders the zirconium oxide ceramic appear lighter yellow after firing. Furthermore, the more times of firing, the more $Pr^{3+}$ will be oxidized into $Pr^{4+}$, such that the zirconium oxide ceramic will appear lighter yellow.

To verify the deduction, the inventors vacuumize the heating device mentioned above, and then heat to perform firing. It turns out the problem that the zirconium oxide ceramic appears lighter yellow is slightly alleviated. However, the effect is not desirable.

The above experiments demonstrate that the deduction of the inventors is reasonable. After vacuumizing the heating device, the oxygen content therein is decreased, thereby the degree of the oxygen vacancies in the polycrystal of zirconium oxide occupied by oxygen atom reduces, rendering less $Pr^{3+}$ being oxidized into $Pr^{4+}$. However, because of the limitation of leakproofness of the heating device, it cannot ensure the oxygen in the heating device is completely removed. The effect is thus not desirable.

To solve the above-problem, the present invention provides a method for post-processing a colored zirconium oxide ceramic. The method can comprise:

putting the colored zirconium oxide ceramic along with a deoxidant into a heating device, and performing a firing process at a preset temperature, wherein the colored zirconium oxide ceramic is obtained by coloring a zirconium oxide ceramic with a colorant containing $Pr^{3+}$, and the amount of said deoxidant is over-stoichiometric with respect to the amount of oxygen in said heating device.

It should be illustrated that the post-processing mentioned in the present invention means performing a process of veneering porcelain and sintering at rising temperature on the zirconium oxide ceramic, performing a process of glazing and sintering at rising temperature, or performing a process of sintering at rising temperature directly without veneering porcelain nor glazing on the zirconium oxide ceramic, or a combination of the various processes mentioned above. A process of the firing mentioned in the present invention means a process of sintering at rising temperature in the post-processing.

It should be illustrated that in the technical solution of the present invention, the parameters for the firing process, such as the temperature of firing, heating rate and holding time, are all the prior art in the field. Those skilled in the art can readily obtain the relevant parameters to achieve the firing process. Thus, no detailed description is needed for the firing process in the present invention. For example, the following parameters can be employed: the temperature of firing is in the range of 700~1050° C., the heating rate is in the range of 30~130° C./min, and the holding time is 0.5~5 min.

Before the firing process, generally the zirconium oxide ceramic still needs to be performed the operation of veneering porcelain or glazing. "Veneering porcelain" or "glazing" mentioned in the present invention can be an operation for simulating tooth enamel texture of patients themselves to superimpose porcelain cement or brush glaze on the surface of the zirconium oxide ceramic. Such operation of "veneering porcelain" of "glazing" is well known technology for those skilled in the art. The present invention will not specifically define it herein. Surely, it can be understood that "veneering porcelain" or "glazing" is not a necessary procedure for the technical solution of the present invention. The post-processing method of the present invention also can be used even without "veneering porcelain" or "glazing" procedure. It should be further illustrated that the heating device mentioned in the present invention can be porcelain furnace, which can be a conventional one in the art, without special requirement. Surely, it can be understood that other heating devices for sintering in the art can also be used. The present invention will not define the heating device herein.

The deoxidant mentioned in the present invention means an organic or inorganic material that can react with oxygen in the heating device to remove oxygen in the heating device, preferably eliminate oxygen in the heating device. It is not necessary to limit the specific type of the deoxidant for the present invention, as long as the deoxidant makes no negative effect on the post-processing and zirconium oxide ceramic. The skilled person in the art can select it based on the actual requirement for production. Preferably, the deoxidant is the organic or inorganic material reacting with oxygen in the heating device, and the resultant thereof is only one or more of $CO_2$, CO and $H_2O$. More preferably, the deoxidant can be selected from at least one of activated carbon, charcoal, starch, coal, saccharose, lactose, polyethylene glycol in powder firm, polyvinyl alcohol, polyethylene, and polypropylene. The deoxidant mentioned in the present invention is commercially available, without any special requirement.

To ensure that oxygen is completely removed, the amount of deoxidant should be over-stoichiometric with respect to the amount of oxygen in said heating device. The specific amount of used deoxidant can be determined by those skilled in the art based on the amount of oxygen in the heating device. For example, when firing is performed by using V5 type porcelain furnace of Beijing Terry Infinite Dental Medical Equipment Co., Ltd, adding only 0.5 g of activated carbon can achieve the purpose of eliminating the oxygen in the porcelain furnace.

"Colored zirconia ceramic" mentioned in the present invention means colored zirconia sintered body with a density of more than 85% of the theoretical density, preferably more than 90% of the theoretical density, more preferably more than 95% of the theoretical density. The particular constitution and structure of the zirconium oxide ceramic are not relevant with the present invention thus the present invention will not illustrate that herein. Those skilled in the art can directly purchase commercial zirconium oxide pre-sintered body to achieve the technical solution of the present invention. For example, UPCERA ST Dental Zirconia. Blank and ST Dental Zirconia Pre-shaded Blank can be selected.

It should be further illustrated that the zirconium oxide pre-sintering body such as ST Dental Zirconia Blank is uncolored during the preparation process. Thus, such a zirconium oxide ceramic block generally needs a coloring treatment before being glazed. For example, UPCERA Coloring Liquid fl purchased from Shenzhen UPCERA Dental Co., Ltd can be used for coloring, and the coloring liquid recited in patent ZL201210558349.8 or others with similar chemical constitution can also be used, followed by firing. During the preparation of pre-sintering body, since the raw materials of the zirconium oxide pre-sintering body such as UPCERA ST Dental Zirconia Pre-shaded Blank have been added with $Pr^{3+}$ oxides for coloring, it is not necessary to perform a recoloring procedure before firing.

It is well known that the commercially available zirconia pre-sintering body such as UPCERA ST Dental Zirconia Blank and ST Dental Zirconia Pre-shaded Blank, has a smaller density and lower strength. Before the firing process is performed by the technical solution of the present invention, a sintering process is generally also required to increase the density to more than 85% of theoretical density, preferably more than 90% of theoretical density more preferably more than 95% of theoretical density. At the moment, the zirconium oxide ceramic shows a higher strength to meet the requirement of the application. The sintering process needs to be operated in the atmosphere containing oxygen. Otherwise, the color presented by sintered zirconium oxide ceramic is too dark to be used. Thus, the technical solution of the present invention will not be applied in this sintering process. Furthermore, although yellow presented by the zirconium oxide ceramic will become slightly lighter in the sintering process, this degree of color change is still acceptable in the sintering process. As long as yellow presented by the zirconium oxide ceramic does not continue to become lighter in the firing process, it will make no effect on the application. That is to say, as long as the conversion of $Pr^{3+}$ to $Pr^{4+}$ is prevented, the color required by the application can be achieved, and coloring the zirconium oxide ceramic yellow can be achieved by completely replacing $Fe^{3+}$ with $Pr^{3+}$.

It is should be further illustrated that it is not necessary to limit whether the zirconium oxide ceramic mentioned in the present invention is machined. This is to say it can be a zirconium oxide ceramic block or a shaped prosthesis rough-body of patient's teeth. Although the zirconium oxide ceramic for dentistry is taken as an example when the present invention describes the zirconium oxide ceramic and in particular examples, it does not mean the present invention is limited to the zirconium oxide ceramic for dentistry. The method of the present invention can be applied for all the zirconium oxide ceramics that are colored with praseodymium oxide and need to remain the color thereof, and this application is within the protection scope of the present invention.

The technical solution of the present application will be described in combination with the following specific examples. The described examples are only part of examples of the present application, not all the examples. Based on the examples in the present application, any other examples obtained by the ordinary skilled person in the art without creative work are within the protection scope of the present application.

Example 1

Dental crown produced from 3Y-TZP zirconium oxide ceramic block was placed into a coloring solution for coloring containing 0.227 mol/L of $Er^{3+}$, 0.005 mol/L of $Pr^{3+}$ and 0.036 mol/L of $Nd^{3+}$, and water as solvent. The sintering process was performed at 1530° C. The density after sintering was 87% of theoretical density. After grinding, polishing and sand blasting the sintered prosthesis rough-body, the prosthesis rough-body was glazed with a glaze paste sold under the trade name e.max Ceram Fluo Glaze Paste (IVOCLAR). The glazed prosthesis rough-body and 0.5 g of activated carbon were then placed on a sintering pan. The glazed prosthesis rough-body was post-sintered in V5+ type porcelain furnace from Beijing Terry Infinite Dental Medical Equipment Co., Ltd with the sintering temperature of 800° C., heating rate of 80° C./min and holding time of 2 min, to obtain the prosthesis.

Comparative Example 1

Compared with example 1, the steps in the comparative example 1 were performed in the same manner as example 1 except no activated carbon was added during the firing process.

The prostheses prepared in example 1 and comparative example 1 were measured by using VITA Easy Shade Colorimeter, respectively. The results were as follows:

The L*, a* and b* values of the prosthesis obtained in example 1 were 79.9, 0.9 and 29.7, respectively. The L*, a* and b* values of the prosthesis obtained in comparative example 1 were 81.9, 0.7 and 19.5, respectively.

Wherein L* represents brightness. It represents black when L*0, white when L*=100, and grey when 0<L*<100. a* represents red when a*>0 or green when a*<0. The larger value of a*, the deeper red it represents, and the smaller value of a*, the deeper green it represents. b* represents yellow when b*>0 or blue when b*<0. The larger value of b*, the deeper yellow it represents, and the smaller value of b*, the deeper blue it represents;

Example 2

Dental crown produced from pre-shaded 3Y-TZP zirconium oxide ceramic block was sintered at 1530° C., and the density after sintering was 90% of theoretical density. Wherein the concentrations of each coloring ion in the pre-shaded 3Y-TZP zirconium oxide ceramic block was $1.02 \times 10^4$ mol/g of $Er^{3+}$, $3.92 \times 10^{-6}$ mol/g of $Pr^{3+}$, and $1.42 \times 10^{-5}$ mol/g of $Nd^{3+}$ respectively. After grinding, polishing and sand blasting the sintered prosthesis rough-body; the prosthesis rough-body was glazed with a glaze paste sold under the trade name e.max Ceram Fluo Glaze Paste (IVOCLAR). The glazed prosthesis rough-body and 1.0 g of charcoal were then placed on a sintering pan. The firing process was performed in the same manner as example 1 to obtain the prosthesis.

Comparative Example 2

Compared with example 2, the steps in comparative example 2 were performed in the same manner as example 2 except no charcoal was added during the firing process.

The prostheses prepared in example 2 and comparative example 2 were measured by using VITA EasyShade Colorimeter, respectively. The results were as follows:

The L*, a* and b* values of the prosthesis obtained in example 2 were 72.5, 4.6 and 45.3, respectively. The L*, a* and b* values of the prosthesis obtained in comparative example 2 were 79.7, 4.1 and 28.6, respectively.

Example 3

Dental crown produced from 3Y-TZP zirconium oxide ceramic block was placed into a coloring solution for coloring containing 0.148 mol/l of $Er^{3+}$, 0.002 mol/l of $Pr^{3+}$ and 0.030 mol/L of Ne, and water as solvent. The sintering process was performed at 1530° C. The density after sintering was 93% of theoretical density. After grinding, polishing and sand blasting the sintered prosthesis rough-body, the prosthesis rough-body was glazed with a glaze paste sold under trade name e.max Ceram Fluo Glaze Paste (IVOCLAR). The glazed prosthesis rough-body and 1.0 g of starch were then placed on a sintering pan. The firing process was performed in the same manner as example 1 to obtain the prosthesis.

Comparative Example 3

Compared with example 3, the steps in comparative example 3 were performed in the same manner as example 3 except no starch was added during the firing process.

The prostheses prepared in example 3 and comparative example 3 were measured by using VITA EasyShade Colorimeter. The results were as follows:

The L*, a* and b* values of the prosthesis obtained in example 3 were 82.3, −1.8 and 21.5, respectively. The L*, a* and b* values of the prosthesis obtained in comparative example 3 were 84.6, −2.1 and 10.1, respectively.

Example 4

Dental crown produced from 3Y-TZP zirconium oxide ceramic block was placed into a coloring solution for coloring containing 0.173 mol/L of $Er^{3+}$, 0.004 mol/L of $Pr^{3+}$ and 0.089 mol/L of $Nd^{3+}$, and water as solvent. The sintering process was performed at 1530° C. The density after sintering was 95% of theoretical density. After grinding, polishing and sand blasting the sintered prosthesis rough-body, the prosthesis rough-body was glazed with a glaze powder sold under trade name DENTAURUM STAINS Universal NEUTRAL. The glazed prosthesis rough-body and 5.0 g of coal were then placed on a sintering pan. The firing process was performed in the same manner as example 1 to obtain the prosthesis.

Comparative Example 4

Compared with example 4, the steps in comparative example 4 were performed in the same manner as example 4 except no coal was added during the firing process.

The prostheses prepared in example 4 and comparative example 4 were measured by using VITA EasyShade Colorimeter, respectively. The results were as follows:

The L*, a* and b* values of the prosthesis obtained in example 4 were 63.6, 7.9 and 35.1, respectively. The L*, a* and b* values of the prosthesis obtained in comparative example 4 were 69.9, 6.2 and 18.9, respectively.

Example 5

Dental crown produced from 3Y-TZP zirconium oxide ceramic block was placed into a coloring solution for coloring containing 0.280 mol/L of $Er^{3+}$, 0.007 mol/L of $Pr^{3+}$ and 0.082 mol/L of $Nd^{3+}$, and water as solvent. The sintering process was performed at 1530° C. The density after sintering was 99.8% of theoretical density. After grinding, polishing and sand blasting the sintered prosthesis rough-body, the prosthesis rough-body and 1.0 g of starch were placed on a sintering pan. The first firing process was performed in the same manner as example 1. After the firing, the first firing prosthesis rough-body was glazed with a glaze powder sold under trade name DENTAURUM STAINS Universal NEUTRAL. The glazed prosthesis rough-body and 3.0 g of saccharose were placed on a sintering pan. The second firing process was performed in the same manner as example 1 to obtain the prosthesis.

Compared with example 5, the steps in comparative example 5 were performed in the same manner as example 5 except the prosthesis rough-body and 1.0 g of starch were not placed on a sintering pan and the firing process was performed in the same manner as example 1.

The prostheses prepared in example 5 and comparative example 5 were measured by using VITA EasyShade Colorimeter, respectively. The results were as follows:

The L*, a* and b* values of the prosthesis obtained in example 5 were 75.2, 4.6 and 44.2, respectively. The L*, a* and b* values of the prosthesis obtained in comparative example 5 were 74.5, 4.7 and 42.8, respectively.

The color of the prosthesis obtained in example 5 was close to that of B4, and the color of the prosthesis obtained in comparative example 5 was close to that of 93. This illustrated that after coloring the prosthesis with B3 coloring liquid and two firing processes by using the technical solution of the present invention, the color can be deepen to close to B4. Since the coloring liquid with lighter color (B3 coloring liquid) can be employed to achieve similar effects as that of the coloring liquid with deeper color (B4 coloring liquid), the amount of pigment in the coloring agent was decreased to improve the transparency of the prosthesis.

Example 6

Dental crown produced from 3Y-TZP zirconium oxide ceramic block was placed into a coloring solution for coloring containing 0.173 mol/L of $Er^{3+}$, 0.004 mol/L of $Pr^{3+}$ and 0.089 mol/L, of $Nd^{3+}$, and water as solvent. The sintering process was performed at 1530° C. The density after sintering was 99.9% of theoretical density. After grinding, polishing and sand blasting the sintered prosthesis rough-body, a porcelain powder under trade name DENTAURUM STAINS Universal NEUTRAL was used for veneering on the prosthesis rough-body and 0.5 g of activated carbon were placed on a sintering pan. The first sintering process was performed by using V5+ type porcelain furnace from Beijing Terry Infinite Dental Medical Equipment Co., Ltd. The sintering temperature was 932° C., heating rate was 55° C./min and holding time was 2 min. After the sintering, the prosthesis rough-body was glazed with a glaze powder under trade name DENTAURUM STAINS Universal NEUTRAL after the first firing. The glazed prosthesis rough-body and 3.0 g of saccharose were then placed on a sintering pan. The second firing process was performed in the same manner as example 1 to obtain the prosthesis with color B3.

It can be seen from the examples of the present invention that after the colored zirconium oxide ceramics is treated by means of the technical solution of the present invention, b* that is used to represent yellow or blue in color parameters for zirconium oxide ceramic is obviously increased. Larger b* means deeper yellow. In the prior art, the technical solution of the present invention solves the problem that when coloring zirconium oxide ceramics with $Pr^{3+}$ instead of $Fe^{3+}$, and then firing the colored zirconium oxide ceramics, it would appear a lighter yellow compared with the color before firing. $Fe^3$ can be completely replaced with Pr?' to color the zirconium oxide ceramic yellow.

The method for post-processing a colored zirconium oxide ceramic provided by the present invention has been described in detail as above. The theory and embodiments of the present invention are illustrated by using specific examples herein. The descriptions of the above examples are only used for helping understand the method and main ideas of the present invention. It should be noted that for those ordinary skilled person in the art, some improvements and modifications can be made to the present invention without departing from the theory of the present invention. These improvements and modifications will also fall into the protection scope of the claims of the present invention.

The invention claimed is:

1. A method for post-processing a colored 3Y-TZP zirconium oxide ceramic, the method comprising:
   putting the colored 3Y-TZP zirconium oxide ceramic along with a deoxidant into a heating device; and
   performing a firing process at a preset temperature,
   wherein the colored 3Y-TZP zirconium oxide ceramic is obtained by coloring a 3Y-TZP zirconium oxide ceramic with a colorant containing $Pr^{3+}$,
   wherein the amount of said deoxidant is over-stoichiometric with respect to the amount of oxygen present in said heating device, and
   wherein the colored 3Y-TZP zirconium oxide ceramic is produced to be a dental prosthesis, and a color of the dental prosthesis is a tooth color of patients.

2. The method according to claim 1, wherein the deoxidant is an organic or inorganic material that can react with oxygen in the heating device for removing oxygen in the heating device.

3. The method according to claim 2, wherein the deoxidant comprises at least one of activated carbon, charcoal, starch, coal, saccharose, lactose, polyethylene glycol in powder form, polyvinyl alcohol, polyethylene, and polypropylene.

4. The method according to claim 1, wherein the method further comprises, before putting the colored 3Y-TZP zirconium oxide ceramic along with the deoxidant into the heating device and performing the firing process at the preset temperature, veneering porcelain or glazing on the colored 3Y-TZP zirconium oxide ceramic.

5. The method according to claim 1, wherein the coloring of the 3Y-TZP zirconium oxide ceramic with the colorant containing $Pr^{3+}$ comprises:
   coloring the 3Y-TZP zirconium oxide ceramic with a coloring agent containing $Pr^{3+}$, or
   coloring the 3Y-TZP zirconium oxide ceramic by means of adding an oxide containing $Pr^{3+}$ into raw materials during preparing of the 3Y-TZP zirconium oxide ceramic.

6. The method according to claim 1, wherein the heating device is a porcelain furnace.

* * * * *